United States Patent [19]

Franz

[11] 3,996,040
[45] Dec. 7, 1976

[54] INCREASING SUCROSE CONTENT OF SUGAR CANE EMPLOYING N-PHENYLSULFONAMIDO-N-PHOSPHONOMETHYL GLYCINE AND CERTAIN DERIVATIVES THEREOF

[75] Inventor: John E. Franz, Crestwood, Mo.

[73] Assignee: Monsanto Company, St. Louis, Mo.

[22] Filed: June 27, 1975

[21] Appl. No.: 591,188

Related U.S. Application Data

[63] Continuation-in-part of Ser. No. 484,056, June 28, 1974, Pat. No. 3,910,969.

[52] U.S. Cl. .................................. 71/87; 71/76
[51] Int. Cl.² .................................. A01N 9/36
[58] Field of Search .................. 71/87, 76

[56] References Cited

UNITED STATES PATENTS

| | | | |
|---|---|---|---|
| 3,205,253 | 9/1965 | Fancher et al. | 71/87 |
| 3,799,758 | 3/1974 | Franz | 71/86 |

OTHER PUBLICATIONS

Porter et al. Chem. Abst. vol. 77 (1972) 160890h.

*Primary Examiner*—Lewis Gotts
*Assistant Examiner*—Catherine L. Mills
*Attorney, Agent, or Firm*—Arnold H. Cole; Donald W. Peterson

[57] ABSTRACT

N-phenylsulfonamido-N-phosphonomethyl glycine and certain derivatives thereof have been found to be useful in the treatment of sugarcane plants to increase their sucrose content.

18 Claims, No Drawings

INCREASING SUCROSE CONTENT OF SUGAR CANE EMPLOYING N-PHENYLSULFONAMIDO-N-PHOSPHONOMETHYL GLYCINE AND CERTAIN DERIVATIVES THEREOF

This application is a continuation-in-part of copending application Ser. No. 484,056, filed June 28, 1974, now U.S. Pat. No. 3,910,969.

U.S. Pat. No. 3,455,675 teaches the use of certain aminophosphonate compounds as herbicides for the destruction of undesired plants. These compounds require three acid groups attached to the nitrogen atom, each through a methylene bridge. One or two of such groups must be phosphonic acid, and the remaining group or groups must be acetic acid. In U.S. Pat. No. 3,556,762 this same class of aminophosphonate compounds is shown to be useful in the treatment of sugarcane to increase its sucrose content. Further, U.S. Pat. No. 3,799,758 teaches that N-phosphonomethyl glycine and certain derivatives thereof, all of which must contain a hydrogen atom on the nitrogen, are also useful as herbicides for the destruction of undesired plants. U.S. Pat. No. 3,853,530 shows that this latter class of compounds also finds utility in the treatment of sugarcane to increase its sucrose content.

This invention relates to a new class of organic chemical compounds. More particularly, this invention is concerned with novel N-substituted derivatives of N-phosphonomethyl glycine and certain amides and esters thereof. The specific derivatives herein are those wherein the hydrogen atom on the nitrogen of said glycine is replaced with a benzenesulfonyl group as defined below. This class of compounds has been found to be useful in the treatment of sugarcane plants to increase their sucrose content.

The compounds of the present invention may be represented by the structural formula

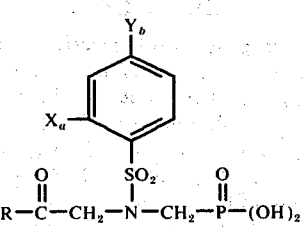

wherein R is hydroxy, lower alkoxy or amino, X and Y are each independently halogen, amino, nitro, methyl, ethyl or methoxy, and a and b are each independently zero or one. The term "lower alkoxy" designates those radicals having straight or branched chains with a total of not more than 4 carbon atoms. It should be understood that when a and/or b are zero, a hydrogen atom is present on the ring carbon.

In general, the N-phenylsulfonamido-N-phosphonomethyl glycines are made by first preparing a solution of about 0.05 mole of N-phosphonomethyl glycine and about 0.1 mole of sodium hydroxide with cooling in an ice bath. A solution of about 0.055–0.075 mole of aromatic sulfonyl chloride in 15–30 ml. of acetone is added, and then a solution of about 0.125 mole of sodium hydroxide in 15 ml. of water is added dropwise over a period of ½ hour. The reaction mixture is then stirred from about 3 hours, filtered, and acidified with concentrated hydrochloric acid. The desired product crystallizes out and is recovered by filtration.

EXAMPLE 1

Following the procedures described above using p-nitrobenzenesulfonyl chloride, the product obtained is N-(p-nitrophenylsulfonamido)-N-phosphonomethyl glycine, sodium salt. Elemental analysis shows 29.09% carbon and 2.63% hydrogen as against calculated values of 28.73% and 2.68% for $C_9H_{10}N_2NaO_9PS$.

EXAMPLE 2

Following the procedures described above using benzensulfonyl chloride, the product obtained is N-phenylsulfonamido-N-phosphonomethyl glycine, sodium salt hydrate, m.p. 260° C. (dec.). Elemental analysis shows 30.71% carbon and 4.0% hydrogen as against calculated values of 30.85% and 3.73% for $C_9H_{13}NNaO_8PS$.

EXAMPLE 3

Following the procedures described above using 2,4-xylenesulfonyl chloride, the product obtained is 98% N-(2,4-xylylsulfonamido)-N-phosphonomethyl glycine, sodium salt, m.p. 270°–275° C. (dec.). Elemental analysis shows 35.93% carbon, 4.10% hydrogen and 6.19% sodium as against calculated values of 36.70%, 4.17% and 6.40% for $C_{11}H_{15}NNaO_7PS$.

EXAMPLE 4

Following the procedures described above using p-chlorobenzensulfonyl chloride, the product obtained is N-(p-chlorophenylsulfonamido)-N-phosphonomethyl glycine, sodium salt, m.p. 267° C. (dec.). Elemental analysis shows 29.37% carbon, 2.97% hydrogen and 6.15% sodium as against calculated values of 29.56%, 2.76% and 6.29% for $C_9H_{10}ClNNaO_7PS$.

EXAMPLE 5

Following the procedures described above using 2-nitro-4-chlorobenzenesulfonyl chloride, the product obtained is N-(2-nitro-4-chlorophenylsulfonamido)-N-phosphonomethyl glycine, hemi-sodium salt, m.p. 278° C. (dec.). Elemental analysis shows 26.76% carbon, 2.41% hydrogen and 2.89% sodium as against calculated values of 27.05%, 2.40% and 2.88% for $C_{18}H_{19}Cl_2N_4NaO_{18}P_2S_2$.

EXAMPLE 6

Following the procedures described above using 2,4-dinitrobenzenesulfonyl chloride, the product obtained is N-(2,4-dinitrophenylsulfonamido)-N-phosphonomethyl glycine, hemi-sodium salt, m.p. 252°–253° C. (dec.). Elemental analysis shows 26.63% carbon, 2.82% hydrogen and 3.68% sodium as against calculated values of 26.35%, 2.33% and 2.80% for $C_{18}H_{19}N_6NaO_{22}P_2S_2$.

EXAMPLE 7

Following the procedures described above using p-anisylsulfonyl chloride, the product obtained is N-(p-anisylsulfonamido)-N-phosphonomethyl glycine, hemi-sodium salt, m.p. 225°–226° C. Elemental analysis shows 33.68% carbon, 3.80% hydrogen and 3.89% sodium as against calculated values of 34.29%, 3.89% and 3.28% for $C_{20}H_{27}N_2NaO_{16}P_2S_2$.

EXAMPLE 8

Following the procedures described above using p-bromobenzenesulfonyl chloride, the product obtained is N-(p-bromophenylsulfonamido)-N-phosphonomethyl glycine, hemi-sodium salt, m.p. 222–225 C. (dec.). Elemental analysis shows 26.98% carbon, 2.69% hydrogen and 2.87% sodium as against calculated values of 27.08%, 2.65% and 2.88% for C H Br N NaO P S

EXAMPLE 9

Following the procedures described above using p-toluenesulfonyl chloride, the product obtained is N-(p-tolylsulfonamido)-N-phosphonomethyl glycine, hemi-sodium salt, m.p. 178–180 C. Elemental analysis shows 36.20% carbon, 4.25% hydrogen and 2.58% sodium as against calculated values of 35.93%, 4.07% and 3.44% for C H N NaO P S

EXAMPLE 10

Following the procedures described above using the reactants of Example 9, the final acidification step is carried out with dilute hydrochloric acid. The product obtained is N-(p-tolylsulfonamido)-N-phosphonomethyl glycine, sodium salt, hemi-hydrate, m.p. 242–247 C. (dec.). Elemental analysis shows 33.91% carbon, 3.97% hydrogen and 6.29% sodium as against calculated values of 33.90%, 3.98% and 6.49% for C H N Na O P S

EXAMPLE 11

Following the procedures described above using o-toluenesulfonyl chloride, the product obtained is N-(o-tolylsulfonamido)-N-phosphonomethyl glycine, hemi-sodium salt hydrate, m.p. 260–263 C. (dec.). Elemental analysis shows 33.19% carbon, 4.25% hydrogen, 6.41% sodium, 3.79% nitrogen and 8.51% phosphorus as against calculated values of 33.06%, 4.16%, 6.33%, 3.86% and 8.53% for C H NHaO PS.

EXAMPLE 12

Following the procedures described above using p-ethylbenzenesulfonyl chloride, the product obtained is a 4:1 mixture of N-(p-ethylphenylsulfonamido)-N-phosphonomethyl glycine and its sodium salt, m.p. 185–190 C. (dec.). Elemental analysis shows 38.77% carbon, 4.76% hydrogen, 3.82% nitrogen and 1.25% sodium as against calculated values of 38.67%, 4.66%, 4.10% and 1.35% for C H N NaO P S

EXAMPLE 13

Following the procedures described above using p-aminobenzenesulfonyl chloride, the product recovered by filtration is further acidified with concentrated hydrochloric acid, and the crystallized product is filtered out. Said product is washed with water and ethanol, then air-dried to obtain N-(p-aminophenylsulfonamido)-N-phosphonomethyl glycine, m.p. 230 C. (dec.). Elemental analysis shows 33.55% carbon, 4.16% hydrogen, 8.57% nitrogen and 9.72% sulfur as against calculated values of 33.34%, 4.04%, 8.64% and 9.89% for C H N O PS.

In general, the alkyl N-phenylsulfonamido-N-phosphonomethyl glycinates are made by first preparing a mixture of about 0.03 mole of alkyl N-phosphonomethyl glycinate, about 0.12 mole of triethylamine and about 100 ml. of acetonitrile. A solution of about 0.033 mole of aromatic sulfonyl chloride in about 25 ml. of acetonitrile is added dropwise, and the reaction mixture is stirred for about 3 hours. Triethylamine hydrochloride is removed by filtration, and the solvent is then removed by evaporation. The residue is taken up in about 75 ml. of 10% sodium bicarbonate, extracted several times with ether and acidified with concentrated hydrochloric acid to yield an oil. The desired product crystallizes from the oil after several days of standing.

EXAMPLE 14

Following the procedures described above using n-butyl N-phosphonomethyl glycinate and p-chlorobenzenesulfonyl chloride, the product obtained is n-butyl N-(p-chlorophenylsulfonamido)-N-phosphonomethyl glycinate, hemi-sodium salt, m.p. 177–179 C. Elemental analysis shows 37.96% carbon, 4.59% hydrogen and 2.84% sodium as against calculated values of 38.01%, 4.54% and 2.80% for C H Cl N NaO P S

EXAMPLE 15

Following the procedures described above using n-butyl N-phosphonomethyl glycinate and p-nitrobenzenesulfonyl chloride, the product obtained is n-butyl N-(p-nitrophenylsulfonamido)-N-phosphonomethyl glycinate, hemi-sodium salt, m.p. 199–201 C. Elemental analysis shows 36.97% carbon, 4.28% hydrogen and 2.60% sodium as against calculated values of 37.06%, 4.43% and 2.73% for C H N NaO P S

EXAMPLE 16

Following the procedures described above using n-butyl N-phosphonomethyl glycinate and p-anisylsulfonyl chloride, the product obtained is n-butyl N-(p-anisylsulfonamido)-N-phosphonomethyl glycinate, m.p. 61–64 C. Analysis shows 42.01% carbon and 5.61% hydrogen as against calculated values of 42.53% and 5.61% for C H NO PS.

EXAMPLE 17

Following the procedures described above using n-butyl N-phosphonomethyl glycinate and p-tolylsulfonyl chloride, the product obtained is n-butyl N-(p-tolylsulfonamido)-N-phosphonomethyl glycinate, hemi-sodium salt, m.p. 146–148 C. Elemental analysis shows 43.13% carbon, 5.61% hydrogen and 3.12% sodium as against calculated values of 43.08%, 5.55% and 2.95% for C H N NaO P S In general, the N-phenylsulfonamido-N-phosphonomethyl glycinamides are made by first preparing a solution of about 0.04 mole of N-phosphonomethyl glycinamide and about 0.04 mole of sodium hydroxide in about 50 ml. of water with cooling in an ice bath. A solution of about 0.04 mole of aromatic sulfonyl chloride in about 15 ml. of acetone is added, and the mixture is stirred while about 0.084 mole of sodium hydroxide in about 15 ml. of water is added dropwise over a period of  hour. The reaction mixture is then stirred for about 3 hours, after which it is acidified with about 98 ml. of concentrated hydrochloric acid, allowed to crystallize overnight and filtered. If crystallization does not occur after standing, the solution is concentrated on a rotary evaporator.

EXAMPLE 18

Following the procedures described above using o-nitrobenzenesulfonyl chloride, the product obtained is N-(o-nitrophenylsulfonamido)-N-phosphonomethyl glycinamide, hemi-hydrate, m.p. 135°–138° C. Elemental analysis gives 29.63% carbon, 3.56% hydrogen and 11.44% nitrogen as against calculated values of 29.80%, 3.59% and 11.60% for $C_{18}H_{26}N_6O_{17}P_2S_2$.

EXAMPLE 19

Following the procedures described above using 2,4-xylenesulfonyl chloride, the product obtained is 98.5% N-(2,4-xylylsulfonamido)-N-phosphonomethyl glycinamide, m.p. 139°–141° C. Elemental analysis gives 38.57% carbon, 4.91% hydrogen and 7.68% nitrogen as against calculated values of 39.29%, 5.10% and 8.33% for $C_{11}H_{17}N_2O_6PS$.

EXAMPLE 20

Following the procedures described above using benzenesulfonyl chloride, the product obtained is N-(phenylsulfonamido)-N-phosphonomethyl glycinamide, m.p. 174°–175° C. Elemental analysis gives 35.00% carbon and 3.93% hydrogen as against calculated values of 35.07% and 4.25% for $C_9H_{13}N_2O_6PS$.

EXAMPLE 21

Following the procedures described above using p-nitrobenzenesulfonyl chloride, the product obtained is N-(p-nitrophenylsulfonamido)-N-phosphonomethyl glycinamide, hemi-sodium salt, m.p. 236°–240° C. (dec.). Elemental analysis gives 29.50% carbon, 3.21% hydrogen and 3.06% sodium as against calculated values of 29.68%, 3.18% for $C_{18}H_{23}N_6NaO_{16}P_2S_2$.

EXAMPLE 22

Following the procedures described above using p-toluenesulfonyl chloride the product obtained is N-(p-tolylsulfonamido)-N-phosphonomethyl glycinamide, m.p. 168°–170° C. Elemental analysis gives 36.99% carbon, 4.71% hydrogen and 8.46% nitrogen as against calculated values of 37.27%, 4.69% and 8.69% for $C_{10}H_{15}N_2O_6PS$.

EXAMPLE 23

Following the procedures described above using p-chlorobenzenesulfonyl chloride, the product obtained is N-(p-chlorophenylsulfonamido)-N-phosphonomethyl glycinamide, m.p. 172°–176° C. Elemental analysis gives 31.43% carbon, 3.46% hydrogen and 8.07% nitrogen as against calculated values of 31.54%, 3.53% and 8.17% for $C_9H_{12}ClN_2O_6PS$.

EXAMPLE 24

Following the procedures described above using p-anisylsulfonyl chloride, the product obtained is N-(p-anisylsulfonamido)-N-phosphonomethyl glycinamide, m.p. 181°–184° C. Elemental analysis gives 35.59% carbon, 4.53% hydrogen and 8.03% nitrogen as against calculated values of 35.51%, 4.47% and 8.28% for $C_{10}H_{15}N_2O_7PS$.

EXAMPLE 25

Following the procedures described above using 2-nitro-4-chlorobenzensulfonyl chloride, the product obtained is N-(2-nitro-4-chlorophenylsulfonamido)-N-phosphonomethyl glycinamide, m.p. 221°–280° C. (dec.). Elemental analysis gives 27.63% carbon, 2.86% hydrogen and 10.53% nitrogen as against calculated values of 27.88%, 2.86% and 10.84% for $C_9H_{11}ClN_3O_8PS$.

EXAMPLE 26

Following the procedures described above using p-bromobenzenesulfonyl chloride, the product obtained is N-(p-bromophenylsulfonamido)-N-phosphonomethyl glycinamide, hydrate, m.p. 234° C. (dec.). Elemental analysis gives 26.50% carbon, 3.34% hydrogen and 7.28% nitrogen as against calculated values of 26.68%, 3.48% and 6.91% for $C_9H_{14}BrN_2O_7PS$.

Example 27

Following the procedures described above using p-fluorobenzenesulfonyl chloride, the product obtained is N-(p-fluorophenylsulfonamido)-N-phosphonomethyl glycinamide, m.p. 175°–178° C. Elemental analysis gives 32.96% carbon, 3.82% hydrogen and 8.43% nitrogen as against calculated values of 33.13%, 3.71% and 8.59% for $C_9H_{12}FN_2O_6PS$.

EXAMPLE 28

A mixture of about 0.01 mole of N-(p-aminophenylsulfonamido)-N-phosphonomethyl glycine (the product of Example 13), 20 ml. of water and about 0.02 mole of sodium hydroxide is concentrated on a steam bath at reduced pressure. The residue is dried in a desiccator at reduced pressure overnight. The product obtained is N-(p-aminophenylsulfonamido)-N-phosphonomethyl glycine,disodium salt, dihydrate, m.p. >300° C. Elemental analysis gives 26.90% carbon, 3.67% hydrogen, 6.79% nitrogen and 11.54% sodium as against calculated values of 26.74%, 3.74%, 6.93% and 11.38% for $C_9H_{15}N_2Na_2O_9PS$.

In determining the appropriate rates and times to apply the compounds of this invention to sugar cane plants, it is necessary to consider both the chronological age of the plant and its stage of maturity since cane, depending upon the practice in different geographical areas, is grown from 9 to about 30 months before harvest. Application at a rate of from about 0.11 to 5.6 Kg. per hectare can be made from about 2 to 8 weeks prior to the projected harvest date. Preferably, such applications are made from 3 to 7 weeks before said date.

An active ingredient of this invention can be conveniently applied to the plants as an aqueous solution or suspension. Said active ingredient can, of course, be in its free acid form, or it may be employed in the form of an alkali metal or amine salt in order to improve such desirable features as solubility or stability. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface active agents which are convenient to use in liquid compositions of this invention are of the non-ionic type such as alkyl phenoxy poly (ethyleneoxy) ethanols, polyethylene oxide adducts of fatty and resin acids, and long chain alkyl mercaptan adducts with ethylene oxide.

A particularly preferred carrier for the acids or salts of this invention is water with about 0.1 to 2.0% by weight of surfactant added thereto. Alternatively, the aqueous carrier can be replaced by a non-toxic mineral oil as such, or as an oil-in-water or water-in-oil emulsion. It has been found convenient to apply the compositions to the plants in the form of aqueous solutions, suspensions or emulsions, the dilution being such that a spray volume of from about 10 to 30 liters of liquid per hectare will contain the desired dosage of active ingredient. It will be recognized, however, that higher or lower total spray volumes can be beneficially employed depending upon the particular dispensing apparatus and other factors well understood by those skilled in the art.

The specific tests which follow are presented as illustrative, non-limiting demonstrations of the useful and unexpected properties of a number of representative compounds of this invention.

TEST PROCEDURE 0.5 Gram of a compound of the invention is dissolved in 4 ml. water that contains as a surfactant about 0.25% (w./w.) nonylphenol which was ethoxylated to contain about 10.5 mols. of ethylene oxide per mol. of nonylphenol ("Tergitol NPX"). 0.6 ml. of this solution is deposited or dropped by means of a syringe with a fine needle on the spindle area at the top of the last visible dewlap of each of 20 stalks of sugar cane. (A dewlap is the junction between the blade of the leaf and the sheath which clasps the stalk). Ten of these stalks were harvested 4 weeks after such treatment and 10 more were harvested 5 weeks after such treatment.

The top 15 joints of the treated cane as well as those of similar untreated cane are removed, combined and analyzed in terms of juice purity and pol percent cane, following the so-called "press method" developed by T. Tanimoto, Hawaiian Planters Record, 57, 133 (1964). "Pol percent cane" is a polarmetric determination and equals the percentage of sucrose if the latter is the only substance in the solution which will rotate the plane of polarized light. In any event, determination of the pol percent cane is a standard and effective method for determining the sucrose content of sugar cane. The results are given below for the treated cane and for the untreated control in each test. The compound employed is indicated by the example number which describes its preparation.

| Treatment | FOUR WEEKS Juice Purity | FOUR WEEKS Pol% Cane | FIVE WEEKS Juice Purity | FIVE WEEKS Pol% Cane |
|---|---|---|---|---|
| Example 2 | 79.21 | 10.35 | 83.42 | 11.74 |
| Control | 77.22 | 9.88 | 69.78 | 7.91 |
| Example 2 | 75.71 | 9.40 | 85.54 | 11.94 |
| Example 3 | 71.97 | 8.34 | 76.53 | 8.79 |
| Example 4 | 4.32 | 8.82 | 74.35 | 8.14 |
| Example 14 | 71.25 | 7.87 | 84.01 | 11.64 |
| Example 15 | 72.89 | 8.55 | 81.38 | 10.12 |
| Example 19 | 75.69 | 8.83 | 77.38 | 9.21 |
| Control | 71.80 | 7.56 | 71.11 | 7.45 |
| Example 16 | 65.63 | 7.15 | 63.62 | 6.71 |
| Example 21 | 57.63 | 5.73 | 67.29 | 7.55 |
| Control | 64.25 | 6.63 | 65.99 | 6.85 |
| Example 28 | 73.31 | 7.97 | 81.17 | 11.62 |
| Control | 71.22 | 7.27 | 70.94 | 8.04 |
| Example 6 | 77.14 | 10.06 | 81.04 | 12.56 |
| Example 8 | 75.25 | 9.52 | 75.56 | 10.11 |
| Example 11 | 71.93 | 9.05 | 77.92 | 10.28 |
| Example 27 | 76.04 | 9.65 | 77.65 | 9.80 |
| Control | 69.39 | 7.57 | 70.07 | 8.24 |

It is apparent that in almost every instance, each reading on the treated sugarcane plants shows an increase over the untreated control. In the few cases where either the earlier or later readings do not indicate improvement, the increase does appear in the other of said readings.

Compositions of this invention generally contain from about 5 to 95 parts active ingredient, about 1 to 50 parts surface active agent and about 4 to 94 parts solvent, all parts being by weight based on the total weight of the composition.

Although the invention has been described herein with respect to specific embodiments, the details thereof are not to be construed as limitations except to the extent defined in the following claims.

What is claimed is:

1. A method for increasing the sucrose content of grown sugar cane which comprises applying to the cane are effective amount of a compound of the formula

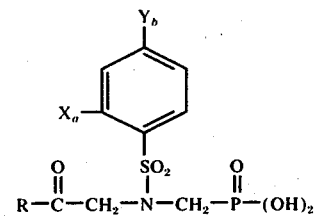

wherein R is hydroxy, lower alkoxy or amino, X and Y are each independently halogen, amino, nitro, methyl, ethyl or methoxy, and a and b are each independently zero or one, said compound being applied to the cane at a time and in an amount effective to increase said sucrose content.

2. A method as defined in claim 1 wherein R is hydroxy.

3. A method as defined in claim 2 wherein a and b are one.

4. A method as defined in claim 3 wherein X and Y are nitro.

5. A method as defined in claim 2 wherein a is zero and b is one.

6. A method as defined in claim 2 wherein a and b are zero.

7. A method as defined in claim 1 wherein R is lower alkoxy.

8. A method as defined in claim 7 wherein a is zero and *b* is one.

9. A method as defined in claim 8 wherein R is n-butoxy and Y is nitro.

10. A method as defined in claim 1 wherein R is amino.

11. A method as defined in claim 10 wherein a and b are one.

12. A method as defined in claim 10 wherein a is zero and b is one.

13. A method as defined in claim 12 wherein Y is amino.

14. A method as defined in claim 1 wherein said compound is applied to the cane from about 2 to 8 weeks prior to harvest.

15. A method as defined in claim 1 wherein said compound is applied to the cane from about 3 to 7 weeks prior to harvest.

16. A method as defined in claim 1 wherein said compound is applied at a rate of about 0.11 to 5.6 kg. per hectare.

17. A method as defined in claim 16 wherein said compound is applied to the cane from about 2 to 8 weeks prior to harvest.

18. A method as defined in claim 16 wherein said compound is applied to the cane from about 3 to 7 weeks prior to harvest.

* * * * *